Jan. 9, 1973 J. T. IRWIN Plant Pat. 3,290
KALANCHOE PLANT
Filed April 13, 1971
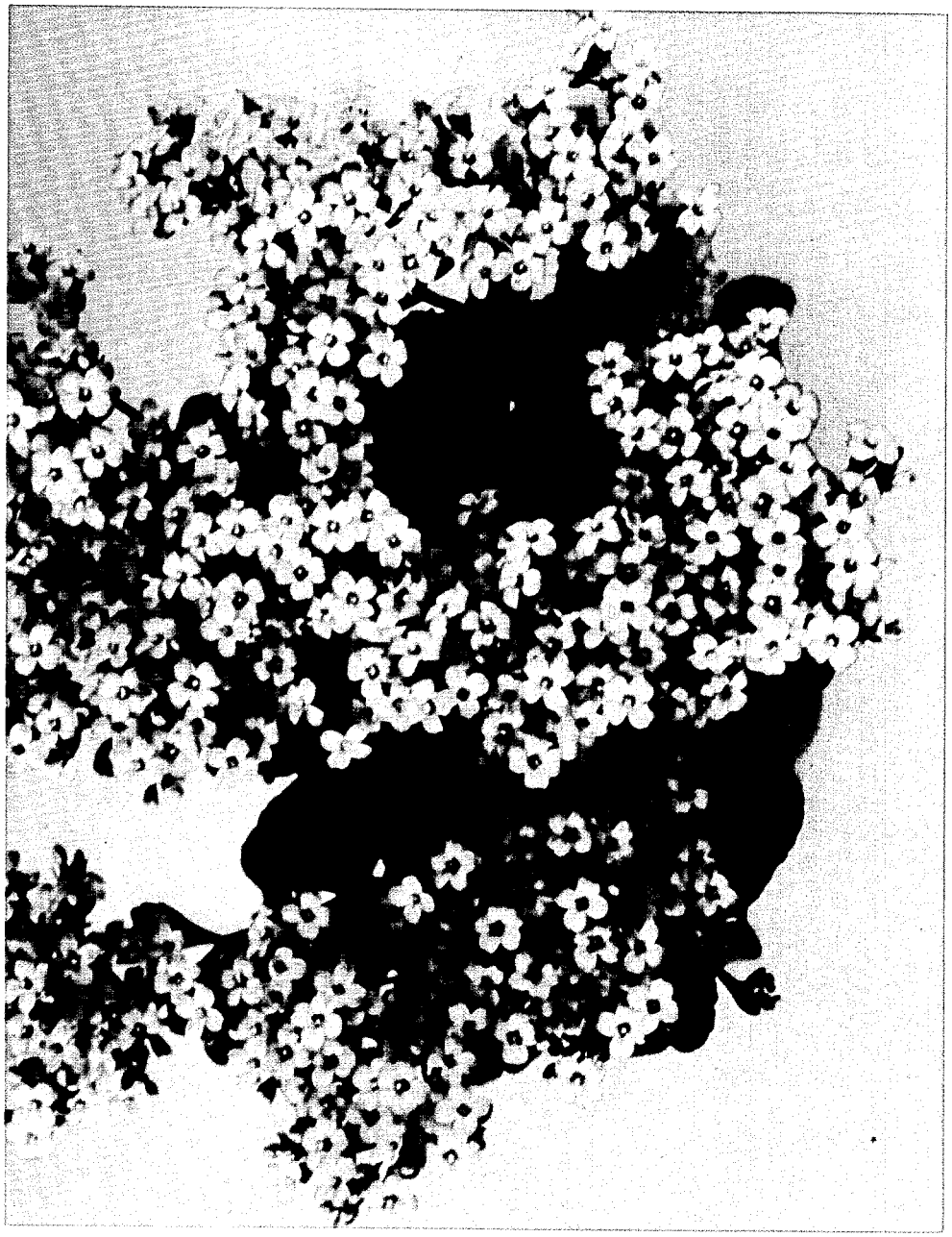
Inventor.
James T. Irwin
By: Robb & Robb
Attorneys.

United States Patent Office

Plant Pat. 3,290
Patented Jan. 9, 1973

3,290
KALANCHOE PLANT

James T. Irwin, Canyon, Tex., assignor to Irwin Greenhouses, Inc., Canyon, Tex.

Filed Apr. 13, 1971, Ser. No. 133,768
Int. Cl. A01h 5/00
U.S. Cl. Plt.—68 1 Claim The present invention relates to a new and distinct variety of kalanchoe plant which was discovered by me as a cultivated sport of the kalanchoe variety known as "Telstar" (unpatented), said discovery having been made by me in one of my greenhouses maintained at Canyon, Tex.

At the time of my discovery, I was commercially growing in my greenhouses located in Randall County, Tex., various varieties of kalanchoe plants, including the variety known as "Telstar" which normally bears flowers of dark pink color. In the course of these growing operations, my attention was attracted to one particular plant among those of "Telstar" which bore flowers of a rose pink color on a very small section of one flowering stem. Close inspection of this particular plant showed that it had sported, and I promptly took steps to carefully preserve the sport and keep it under close observation. A few months later, I asexually reproduced the sport in my greenhouses aforesaid by rooting of stem tip cuttings taken from the sport. After flowering of the latter, the best plant was selected and put under lights to induce vegetative growth. Again after flowering, the best selection was made for further asexual reproduction by rooted cuttings taken therefrom and propagated by me in my commercial greenhouses in Randall County. Continued observations and tests of the original sport and its progeny subsequently derived therefrom, fully confirmed that the rose pink flower color comes true and remains stable as a new, distinctive and commercial valuable kalanchoe flower color. I am convinced that my new sport is definitely a new and distinct kalanchoe variety, as evidenced by the following unique combination of features, including the new flower color, which are outstanding therein and which distinguish the same from its parent "Telstar," as well as from all other kalanchoe varieties of which I am aware:

(1) A compact but upright and medium tall habit of growth;

(2) Attractive glossy dark green foliage of medium to small size which accentuates the attractiveness of the flower heads and contributes to good shipping qualities;

(3) A compact and clean-cut flower form with the flower petals being decidedly notched at their tips and having an obtuse form;

(4) A distinctive and attractive rose pink flower color which is uniquely different from other kalanchoe varieties; and (5) An ability to be brought into bloom all year around by appropriately adjusting the photoperiod.

The accompanying drawing shows a typical specimen plant of my new kalanchoe variety as depicted in bloom and in color as nearly true as it is reasonably possible to make the same in an illustration of this character.

The following is a detailed description of my new kalanchoe variety, with color terminology in accordance with Maerz and Paul Dictionary of Color, except where general color terms of ordinary dictionary significance are obvious:

Parentage: Sport of "Telstar."

Propagation: Holds its distinguishing characteristics through succeeding propagations by direct rooting of stem tip cuttings.

Locality where grown and observed: Randall County, Tex.

Plant:

*Form.*—Upright; compact.

*Growth habit.*—Medium vigorous; upright; compact.

*Rooting habit.*—Numerous fibrous roots; roots easily from any part of stem.

*Blooming habit.*—Compound umbel.

*Blooming season.*—Normally about January 1 to January 5, but suitable for forcing into year-around bloom by appropriate photoperiod adjustment in greenhouse.

Foliage:

*Size.*—Medium small. Young—about 1 to 1½ inches x 1½ inches to 2 inches. Mature—about 2½ inches x 3½ inches.

*Quantity.*—Normal.

*Color.*—New foliage—upper side—Green, No. 84—. Under side—Green, No. 83. Old foliage—Upper side—Green, No. 83+. Under side—Green, No. 83—.

*Shape.*—Obovate. Base—from acute to obtuse. Tip—obtuse.

*Texture.*—Upper side—glossy; smooth. Under side—smooth.

*Edge.*—Mildly crenate.

*Aspect.*—Glossy; fleshy.

Disease resistance: More resistant to common kalanchoe diseases, as evidenced by complete absence of any disease problems in comparison with other varieties grown under the same conditions in Randall County, Tex.

Flowers: Complete.

*Size.*—About ⅝ inch in diameter and about ⅜ inch deep, with pronounced sepals; petals about 7/32 inch long and about 7/32 inch wide.

*Form.*—Perigynous; 4-parted calyx, corolla and pistil; 8 stamens; section petals united; ovary inferior.

*Color.*—Upper side—newly opened petals—Rose Pink, No. 37. Older petals—Rose Pink, No. 37—. Under side (newly opened and older petals)—Rose Pink, No. 37, with some Green, No. 81+ extending slightly from base into under side of petal.

*Blooming period.*—From 4 to 6 weeks.

Hardness: Good; has successfully withstood temperatures as low as 35°–40° F. and as high as 105°–110° F. as grown and observed in Canyon, Tex.

General observations: While the rose pink flower color of my new kalanchoe variety is its most unique and distinctive feature, its attractiveness and daintiness are enhanced by the fact that the flower petals are shorter than those of its parent "Telstar," giving them a more compact and cleaner-cut appearance and form as borne on short and stocky stems, with much-branching of the flower heads; in general, the plant of my new variety is slightly more compact than "Telstar," its leaves are somewhat smaller in size and better accentuate the attractiveness of the flowers, and the flower petals are notched at their tips so that they have an obtuse form contrary to the acute petal form typical of "Telstar."

I claim:

1. A new and distinct variety of kalanchoe plant, substantially as herein shown and described, characterized particularly as to novelty by the unique combination of a compact but upright and medium tall habit of growth, attractive glossy dark green foliage of medium to small size which accentuates the attractiveness of the flower heads and contributes to good shipping qualities, a compact and clean-cut flower form, with the flower petals being decidedly notched at their tips and having an obtuse form, a distinctive and attractive rose pink flower color which is uniquely different from other kalanchoe varieties, and an ability to be brought into bloom all year around by appropriately adjusting the photoperiod.

No references cited.

ROBERT E. BAGWILL, Primary Examiner